United States Patent [19]
Moshe et al.

[11] Patent Number: 6,025,724
[45] Date of Patent: Feb. 15, 2000

[54] DEVICE AND METHOD FOR DETERMINING THE MOISTURE CONTENT OF PACKAGED MATERIAL

[75] Inventors: Danny S. Moshe, Kiryat Ono; Alexander Greenwald, Nazareth-Illit, both of Israel

[73] Assignee: Malcam Ltd., Tel Aviv, Israel

[21] Appl. No.: 08/974,983

[22] Filed: Nov. 20, 1997

[51] Int. Cl.[7] .................................................. G01N 23/00
[52] U.S. Cl. ........................... 324/640; 324/643; 324/634
[58] Field of Search ..................................... 324/640, 643, 324/634; 73/73

[56] References Cited

U.S. PATENT DOCUMENTS

| | | |
|---|---|---|
| 2,659,860 | 11/1953 | Breazeale . |
| 3,360,721 | 12/1967 | Pullman . |
| 3,644,826 | 2/1972 | Cornetet, Jr. . |
| 3,810,005 | 5/1974 | Bennion et al. . |
| 3,815,019 | 6/1974 | Wiles . |
| 3,829,764 | 8/1974 | Bosisio . |
| 4,352,059 | 9/1982 | Suh et al. . |
| 4,361,801 | 11/1982 | Meyer et al. . |
| 4,500,835 | 2/1985 | Heikkila . |
| 4,546,311 | 10/1985 | Knochel . |
| 4,578,998 | 4/1986 | Gard . |
| 4,675,595 | 6/1987 | Hane . |
| 4,789,820 | 12/1988 | Parrent, Jr. et al. . |
| 4,962,384 | 10/1990 | Walker . |
| 4,991,915 | 2/1991 | Thompson et al. . |
| 5,333,493 | 8/1994 | Cutmore . |
| 5,581,191 | 12/1996 | Yamaguchi . |
| 5,619,143 | 4/1997 | Stevens et al. . |
| 5,621,330 | 4/1997 | Greenwald et al. . |

*Primary Examiner*—Josie Ballato
*Assistant Examiner*—Jose M. Solis
*Attorney, Agent, or Firm*—Mark M. Friedman

[57] ABSTRACT

A method of determining the moisture content of material on a bobbin featuring a hollow core, the method comprising the steps of: (a) transmitting a plurality of microwaves substantially through a portion of the bobbin, such that the microwaves are transmitted microwaves; (b) receiving the transmitted microwaves such that the microwaves are received microwaves; (c) determining a phase shift and an attenuation from the received microwaves; (d) repeating steps (a) to (c) for at least a portion of the material on the bobbin, such that a plurality of phase shifts and a plurality of attenuations is obtained; (e) using at least one empirical factor selected from the group consisting of weight of the bobbin, temperature of the bobbin, shape of the bobbin and type of the material to correct the plurality of attenuations, producing a plurality of corrected attenuations; (f) calculating a raw moisture content of the material from the corrected attenuations; (g) correcting the plurality of phase shifts for an artefact caused by the hollow core, such that the plurality of phase shifts becomes a plurality of corrected phase shifts; (h) determining a density of the material from the corrected phase shifts; and (i) calculating a final moisture content of the material from the density and from the raw moisture content.

9 Claims, 10 Drawing Sheets

DEVICE AND METHOD FOR DETERMINING THE MOISTURE CONTENT OF PACKAGED MATERIAL

FIELD AND BACKGROUND OF THE INVENTION

The present invention relates to a device and method for determining the moisture content of material which is held on a bobbin or cone and, more particularly, to a device and method for determining the moisture content of non-homogeneous material held in a structure which contains a hollow core. Many different types of synthetic and organic materials are the basis for the construction of many different manufactured products. These materials must be gathered, transported and stored before being used in the manufacturing process. The manufacturing process itself may require multiple procedures, first to prepare the raw material, and then to use the processed material in the formation of the actual product. Many of these procedures are dependent upon the moisture content of the material. If the moisture content is too high, for example, the material may decompose during storage and transportation, before it can be used. If the moisture content is too low, processing and use of the material may be difficult.

Synthetic and organic materials whose behavior depends upon their moisture content include cotton, paper, wool, seeds, pharmaceuticals and synthetic fibers. As an example, cotton can be considered, although it will be appreciated that similar examples could be given for any of the above materials. Cotton is processed to separate the desired cotton from contaminating materials such as seeds, and is then spun into fibers for use in textile manufacture. For such processing and spinning to be successful, the cotton fibers should have an even moisture content that is neither too high nor too low. For example, fibers with low moisture content are weaker, breaking more frequently.

The optimum moisture content of the cotton fibers for the production of textiles is from 6.5 to 8% before spinning and between 6–10% on the cones or bobbins, depending upon the requirements of the subsequent processing steps. Thus, effective moisture control in the textile mill depends upon accurate measurement of the moisture content of the fibers.

The internal structure of the bobbin itself presents difficulties for measuring the moisture of material wrapped around it. The layers of the fibers around the bobbin frequently are not parallel, which can artifactually alter the behavior of the transmitted beam, and hence the apparent moisture content of the bobbin. Thus, the internal structure of the bobbin must be compensated for during calculation of the moisture content of the material.

In order to compensate for all of these potential measurement artefacts, moisture measurements may be performed using microwave radiation. Typically, a microwave radiation source is located on one side of the cotton bobbin, and an antenna is located on the opposite side of the bobbin. The radiation source beam is transmitted through a portion of the bobbin and is received by the receiving antenna, which then produces a signal. This signal is used to determine the moisture content of that portion of the bobbin and the mass uniformity of the bobbin. A method for performing such moisture measurements is disclosed in U.S. Pat. No. 5,621,330, referenced herein as if incorporated in full.

However, such measurements are difficult to perform because of the structure of the bobbin itself. Cotton bobbins typically have a hollow core. This hollow core significantly interferes with measurements made by microwave radiation and reduces the effectiveness of prior art devices and methods. Furthermore, cotton fibers on bobbins still have many irregularities of internal structure of the fibers themselves, making measurements of the moisture significantly more difficult. Hereinafter, the term "bobbin" refers to a structure of substantially any three-dimensional shape which has a hollow core.

Of course, cotton is not the only material to be transported, stored and processed on bobbins. Paper, pharmaceuticals, wool fibers, silk fibers and synthetic fibers are also necessary synthetic and organic materials which form the basis of many different products. Each of these materials may also be transported and stored on bobbins. The moisture content of each can affect processing, storage and manufacture. Furthermore, each of these materials forms different structures. That is, a bobbin of paper may have a very different internal structure from a bobbin of cotton. Thus, a moisture measuring device must be able to compensate for the effect of all of these different types of structures on the measured moisture content.

There is thus a widely recognized need for, and it would be highly advantageous to have, a device for measuring the moisture content of a bobbin of material, which can compensate for the hollow core of the bobbin, which can also determine the internal structure of the material and which is capable of adjusting such measurements for the material itself.

SUMMARY OF THE INVENTION

According to the present invention there is provided a method of determining the moisture content of material on a bobbin featuring a hollow core, the method comprising the steps of: (a) transmitting a plurality of microwaves substantially through a portion of the bobbin, such that the microwaves are transmitted microwaves; (b) receiving the transmitted microwaves such that the microwaves are received microwaves; (c) determining a phase shift and an attenuation from the received microwaves; (d) repeating steps (a) to (c) for at least a portion of the material on the bobbin, such that a plurality of phase shifts and a plurality of attenuations is obtained; (e) using at least one empirical factor selected from the group consisting of weight of the bobbin, temperature of the bobbin, shape of the bobbin and type of the material to correct the plurality of attenuations, producing a plurality of corrected attenuations; (f) calculating a raw moisture content of the material from the corrected attenuations; (g) correcting the plurality of phase shifts for an artefact caused by the hollow core, such that the plurality of phase shifts becomes a plurality of corrected phase shifts; (h) determining a density of the material from the corrected phase shifts; and (i) calculating a final moisture content of the material from the density and from the raw moisture content. Preferably, the material features an internal structure and an irregularity of the internal structure is calculated by comparing one of the plurality of corrected phase shifts to a previous value of the corrected phase shifts, such that the irregularity is detected if one of the plurality of corrected phase shifts differs from the previous value. More preferably, the irregularity of the internal structure indicates that the material includes more than one type.

Preferably, the at least one empirical factor is a plurality of empirical factors, and the factors are stored in a database. Also preferably, the plurality of corrected attenuations is corrected according to a non-deterministic algorithm, the algorithm using the empirical factors to correct the attenuations. More preferably, the material is selected from the group consisting of cotton fiber, silk fiber, wool fiber, pharmaceutical, paper and synthetic fiber. Preferably, the step of determining the density includes detecting a defect in the material, the defect being selected from the group consisting of irregular moisture distribution within an interior of the material and presence of a foreign body inside the material.

According to another embodiment of the present invention, there is provided a method for determining a moisture content of material in a module, the method comprising the steps of: (a) transmitting a plurality of microwaves of a plurality of frequencies substantially through a portion of the material in the module, the microwaves of each of the plurality of frequencies being transmitted sequentially such that the microwaves are transmitted microwaves of a particular frequency; (b) receiving the transmitted microwaves of the particular frequency such that the microwaves are received microwaves of the particular frequency and such that the transmitted microwaves from the plurality of frequencies are received; (c) determining an attenuation from the received microwaves of each of the particular frequencies, such that a plurality of attenuations is determined; (d) determining the moisture content of the portion of the material from the plurality of attenuations; and (e) repeating steps (a) to (d) to determine the moisture content of a plurality of portions of the material on the module.

Preferably, the attenuation is determined by adjusting for a linear effect of the plurality of frequencies, such that the attenuation is directly proportional to each of the plurality of frequencies. Also preferably, the moisture content is directly proportional to a summation of the plurality of attenuations. More preferably, the summation of the plurality of attenuations is divided by a correlation factor, the correlation factor being empirically determined from a type of material and a structure of the module.

According to preferred embodiments of the present invention the method further comprises the steps of: (f) determining a phase shift from the received microwaves of each of the particular frequencies, such that a plurality of phase shifts is determined; (g) determining a density of the material from the plurality of phase shifts; and (h) repeating steps (a) to (g) to determine the density of a plurality of portions of the material on the module. Preferably, the density of the material is determined by linear regression fitted to the plurality of phase shifts according to an empirical function, the empirical function being selected according to a type of the material and a structure of the module. Alternatively and more preferably, the density of each of the plurality of portions of the material is compared to the density of each other of the plurality of portions of the material to determine a regularity of a structure of the material in the module, the structure being irregular if the densities are substantially different. Also more preferably, the moisture content of the plurality of portions of the material is adjusted according to the regularity of the structure.

Hereinafter, the term "material" includes any material which can be stored on a bobbin or any other hollow-core structure. For example, cotton, wool, silk and synthetic fibers, as well as paper, can all be stored on bobbins. Pharmaceutical materials, such as powdered medications, can also be stored on a "bobbin", although such a bobbin would probably be a box of powder with a hollow core. Hereinafter, the term "bale" refers to any structure in which material is present in pressed layers and tied with ties wrapped around the structure. Hereinafter, the term "module" refers to any structure of material, including bales and bobbins.

BRIEF DESCRIPTION OF THE DRAWINGS

The invention is herein described, by way of example only, with reference to the accompanying drawings, wherein.

DESCRIPTION OF THE PREFERRED EMBODIMENTS

The present invention is of a method and a device which can be used to measure the moisture content and the internal structure of material on a bobbin with a hollow core.

The principles and operation of a method and a device according to the present invention may be better understood with reference to the drawings and the accompanying description.

Figure 1A:
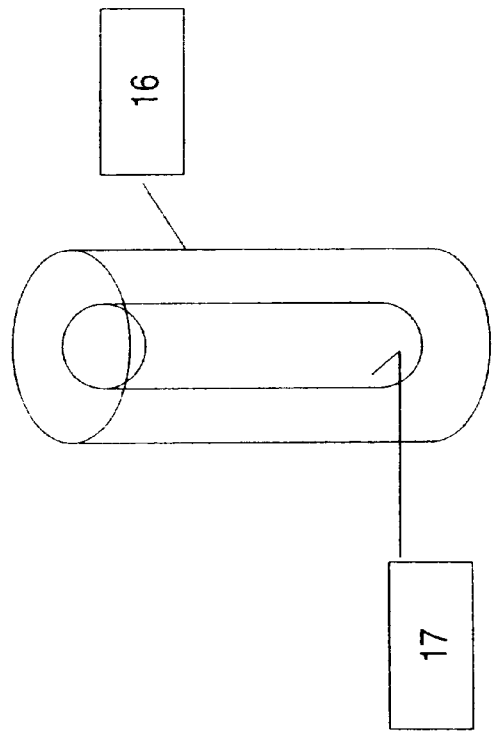
FIGS. 1A and 1B are illustrative examples of material on bobbins whose moisture can be measured by the method of the present invention.
Figure 1B:
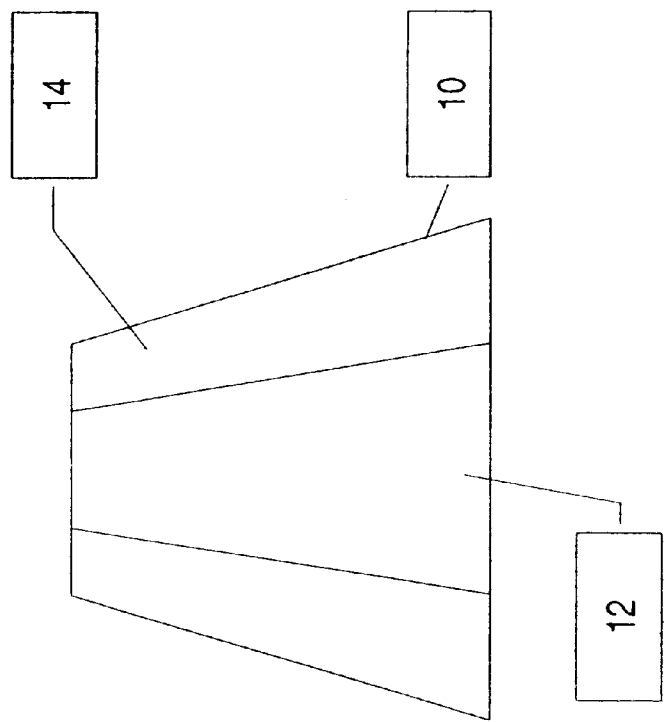

Referring now to the drawings, FIGS. 1A and 1B are illustrative examples of material stored on bobbins with hollow cores. FIG. 1A shows an internal view of a bobbin 10 with a hollow core 12. The term "hollow core" includes any substantially hollow space or area, containing any substance which is not a continuous solid. This substance could include air or another gas or gases, a vacuum, polymerous fibers, sand or other particulate matter, or a liquid, for example. For purposes of clarity only, the following discussion will center around hollow cores which contain air.

A plurality of layers of material 14 are wrapped around bobbin 10. Layers 14 can be any synthetic or organic material, such as cotton fibers for example. The following discussion will mainly focus on bobbins with cotton fibers, it being understood that this is for purposes of discussion only and is not meant to be limiting in any way.

Layers 14 have an internal structure which can be somewhat irregular, in the sense that the density of the material can vary. FIG. 1B shows an internal view of a second bobbin 16 in the shape of a cylinder. Bobbin 16 also has hollow core 12 and layers of material 14, which can be sheets of paper, for example. It should be noted that the term "layers" includes both individual sheets and individual fibers, as well as groups of these individual sheets and fibers.

Figure 2:
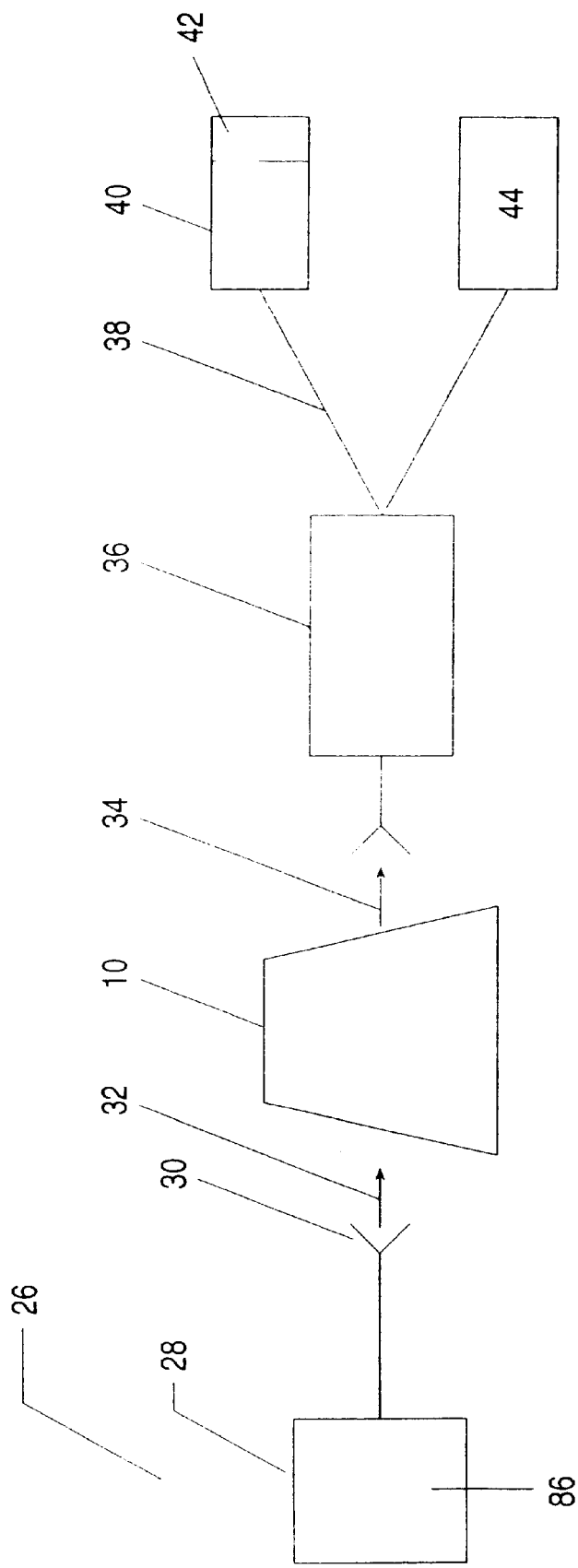
FIG. 2 is a block diagram illustrating one embodiment of a device which can be used with the method of the present invention.

FIG. 2 shows an exemplary device for performing the moisture measurements of the present invention. It should be noted that this device is given for illustrative purposes only and is not meant to be limiting. Device 26 includes a microwave radiation source 28, shown on one side of bobbin 10. Microwave radiation source 28 preferably includes at least one source antenna 30 for transmitting a source beam 32. Source beam 32 is directed through bobbin 10, and passes out of bobbin 10 as an exit beam 34. Exit beam 34 is received by at least one receiving antenna 36. Receiving antenna 36 is located on a substantially opposing side of bobbin 10 relative to source antenna 30.

After receiving antenna 36 has received exit beam 34, receiving antenna 36 produces an antenna signal 38. Antenna signal 38 then goes to an attenuation unit 40. Attenuation unit 40 includes an attenuation measurer 42, which measures the attenuation of antenna signal 38. As source beam 32 passes through bobbin 10, source beam 32 is attenuated. The extent of this attenuation is determined by the elementary mass, which is the mass of the material of bobbin 10 encountered by source beam 32, and by the moisture content of the material of bobbin 10 encountered by source beam 32. Thus, attenuation measurer 42 is actually measuring the extent to which source beam 32 is attenuated by passing through bobbin 10.

At least a part of antenna signal 38 also goes to a phase shift determiner 44, which determines the phase shift of antenna signal 38. This phase shift is actually the phase shift caused by source beam 32 passing through bobbin 10, so that the phase shift is the difference between the phase of source beam 32 and the phase of exit beam 34. The attenuation and the phase shift are then determined.

Microwave radiation source 28 can also optionally include a number of features which are designed to maximize the sensitivity of the moisture content measurements, by manipulating the direction of the electric field density of source beam 32. Microwave radiation source 28 can include an electric field director 86. Electric field director 86 determines a direction of the electric field density of source beam 32 relative to bobbin 10, such that the direction of the electric field density partially determines the magnitude of the attenuation and the magnitude of the phase shift. If bobbin 10 has layers 14 (not shown), substantially the maximum attenuation and substantially the maximum phase shift of antenna signal 38 is obtained when the electric field density is substantially perpendicular to layers 14 (not shown) of bobbin 10. When the electric field density is substantially parallel to layers 14 (not shown) of bobbin 10, substantially the minimum attenuation and the minimum phase shift of antenna signal 38 is obtained. Even if bobbin 10 does not have layers 14, changing the direction of the electric field density will still alter the attenuation and phase shift of antenna signal 38, according to the orientation of the material being measured relative to the electric field density. Electric field director 86 determines the direction of the electric field density according to feedback from attenuation measurer 42. Thus, if the attenuation of antenna signal 38 is low, electric field director 86 can change the direction of the electric field density in order to compensate. Clearly, this has obvious advantages in maximizing the sensitivity and accuracy of the moisture measurements.

Figure 3:
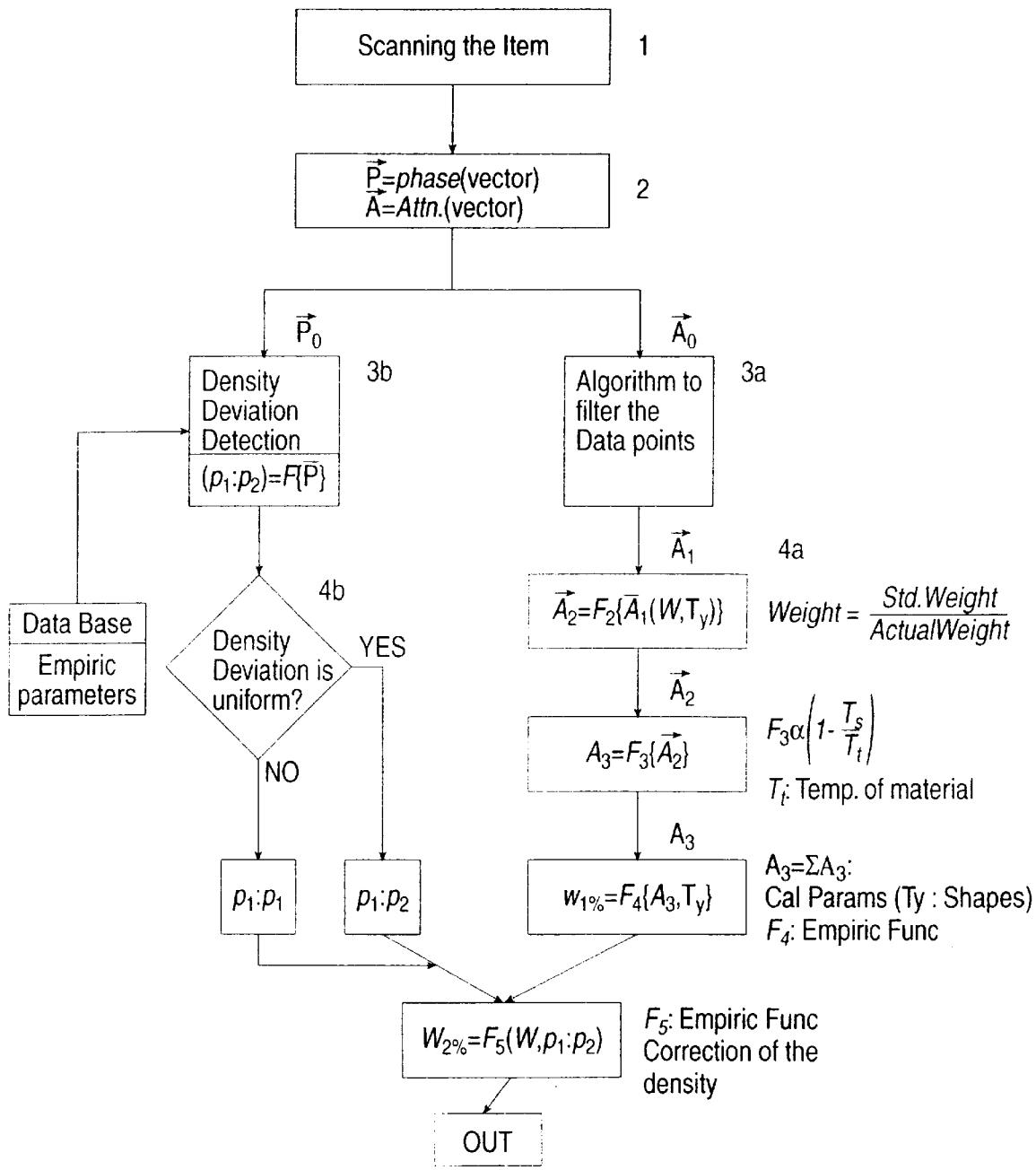
FIG. 3 is a flow chart of the method of calculating the moisture content of the material.

The attenuation and the phase shift of antenna signal 38 are then used by a moisture determiner 46 to determine the moisture content of bobbin 10. FIG. 3 shows a flow chart of the calculations for determining the moisture content and the internal structure of the material on the bobbin. The attenuation is used to determinine the raw moisture content of the material, while the phase shift is used to determine the internal structure of the material. Both the attenuation and the phase shift are used in combination with empirically determined correction factors to calculate the final moisture content of the material.

The first step in the flow chart is the scanning of the material, which can be performed using the device essentially as described above. The material is scanned by transmitting a plurality of microwaves through the bobbin so that they pass through the bobbin and are received on the other side. From this scanning, step, the phase shift and the attentuation are calculated, as shown in step 2. The flow chart now branches into two parts. The right branch shows the steps used in calculating the raw moisture content of the material, while the left branch shows the steps for the determination of the internal structure of the material. For clarity, steps in the right (moisture content) branch will have the letter "a" appended; e.g., "3a", "4a", etc. Steps in the left (internal structure) branch will have the letter "b" appended; e.g., "3b", "4b", etc.

Figure 7A:
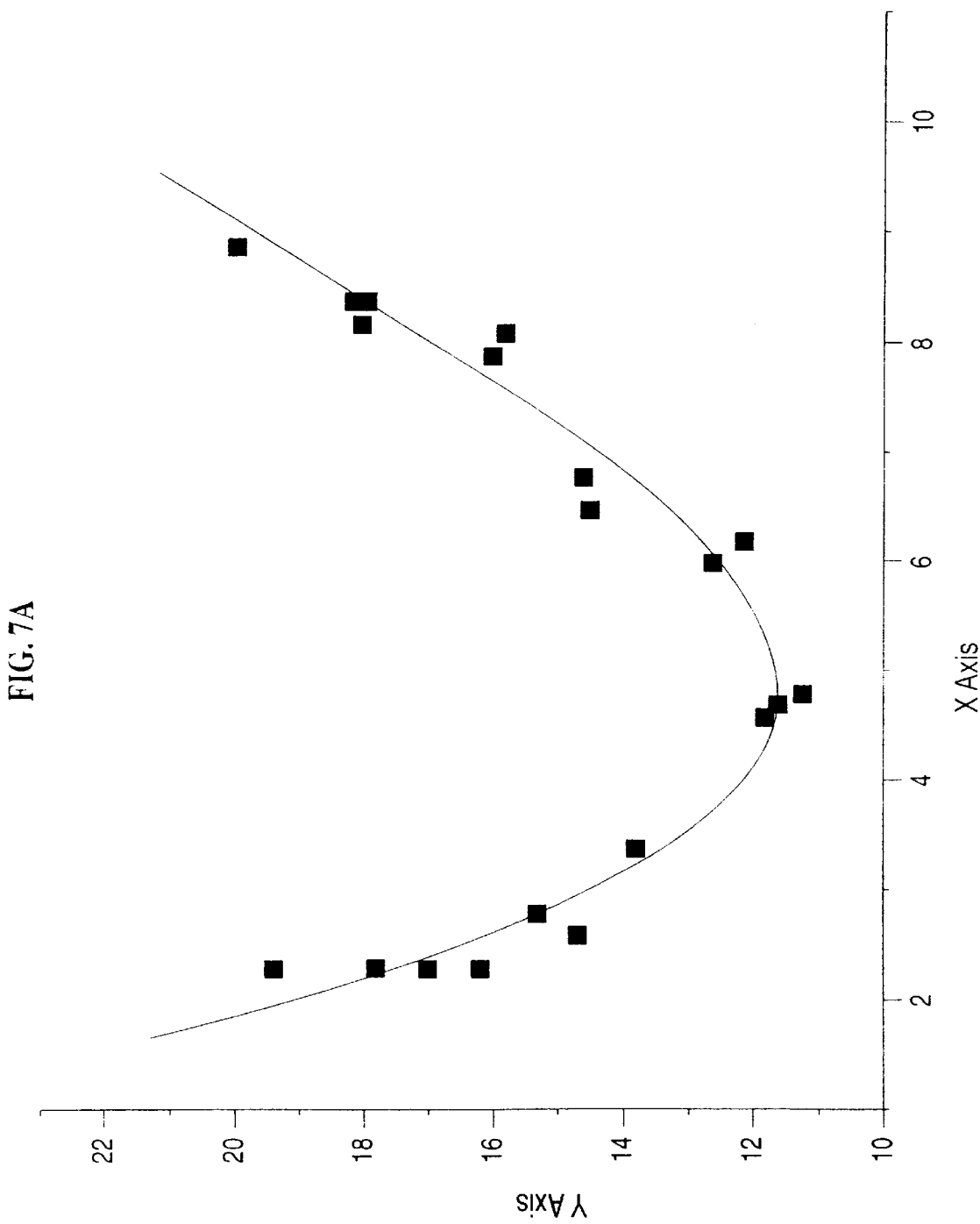
FIGS. 7A and 7B show examples of data curves used for calculating the moisture content according to the present invention.
Figure 7B:
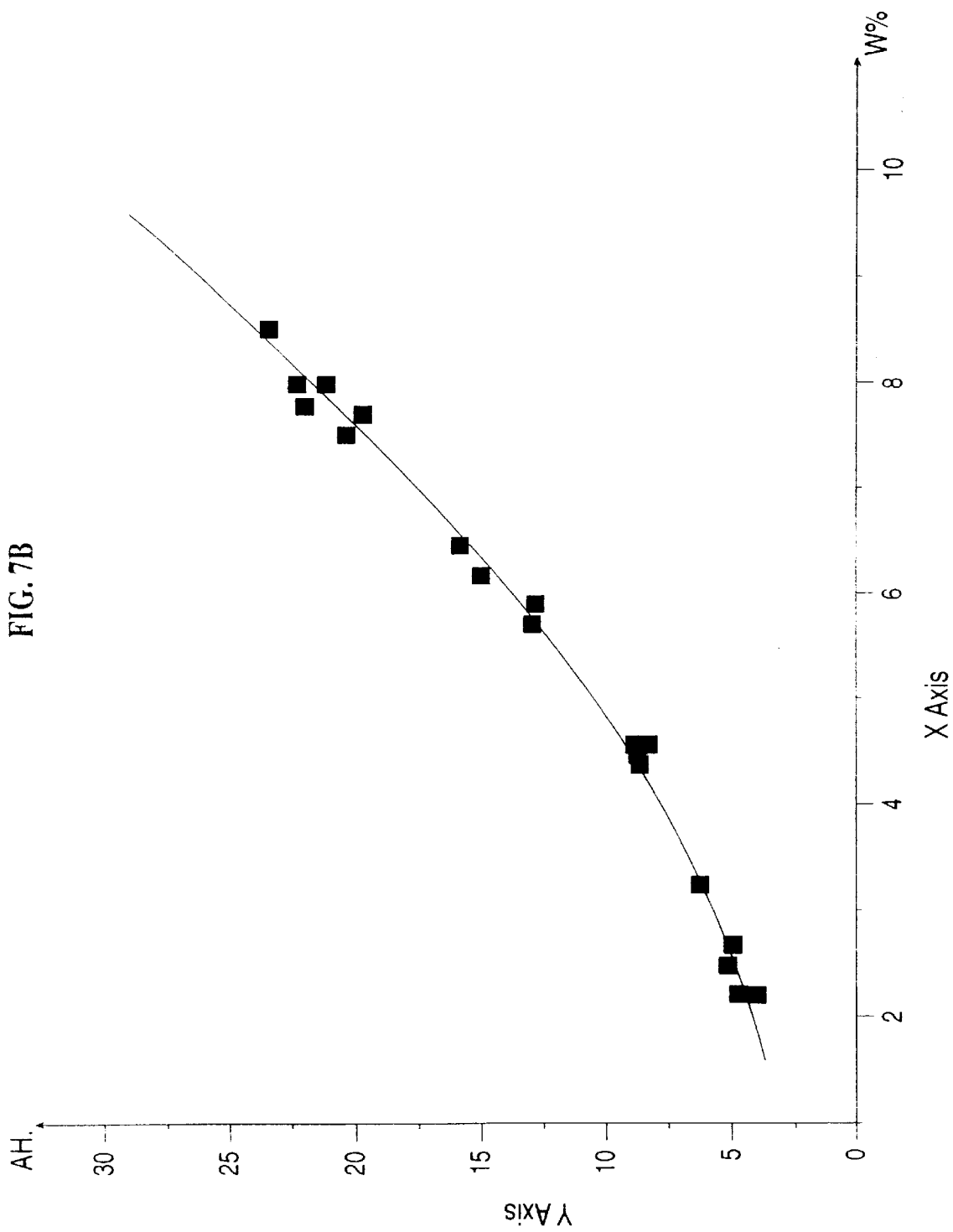

Following the right branch, in step 3a an algorithm is used to filter the data points obtained for the attenuation. Each time a measurement of the attentuation is made as described above in FIG. 2, a data point is obtained. These data points must be filtered as shown in FIGS. 7A and 7B below, since otherwise artefactual data could be obtained.

Once the data has been filtered, the attenuation is corrected for the effect of the weight of the material and the bobbin, as shown in step 4a. This correction is based upon an empirically determined factor and produces a weight-corrected attenuation value. Next, in step 5a, the weight-corrected attenuation value is corrected for temperature, to produce a temperature-corrected attenuation value. The function for this correction is proportional to $1-T_s/T_e$, where $T_s$ is the standard temperature, and $T_e$ is the measured temperature. The temperature-corrected attenuation value thus is compensated for the effect of measurements at different temperatures.

In step 6a, the complete set of all temperature-corrected attenuation values from a single slice of material is used to calculate a raw moisture value for that slice. This calculation is performed according to a function which can be a linear integration of all the temperature-corrected attenuation values or else a polynomial, depending upon such empirical factors as the type of material being measured, the shape and structure of the bobbin itself. In any case, these empirical factors are included in the calculation, so that their effects on the measurement can be compensated for. This raw moisture value will be used in the determination of the final moisture value for the slice of material. However, the final moisture value cannot be determined without knowing the density of material, which is calculated as shown in the left branch of the flow chart.

Figure 5A:
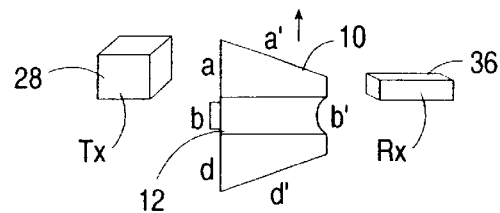
FIGS. 5A–5D show the calculations of FIG. 3 in greater detail for a parallel bobbin.

Turning back now to the left branch, which includes steps for calculating the density of the material, the density is calculated from the phase shift, in accordance with empirical information from a database. The empirical information includes the type of material and the structure of the bobbin itself, as well as the location of the bobbin relative to the antenna and transmitter. The location is particularly important because the density of the bobbin chances depending upon the cross-sectional slice which is examined. For example, if the bobbin is lying on its side as shown in FIG. 5A, a slice taken through points a–a' will include only the material on the bobbin. However, a slice taken through points b–b' will also include the hollow core, which can significantly alter the phase shift and hence the calculated density. Thus, the relative location of the measured slice of material is included in the caculation of the density.

Additionally, the database preferably contains "fuzzy descriptors" which are used to find the correct phase region and to determine the proper relationship between measured phase shift values and calculated density values. These "fuzzy descriptors" are obtained by collecting phase shift data from an analysis of a test shape having known features, and then comparing the calculated density values with the true, known density values of the test shape. From this analysis of the test shape, the proper correlation between the measured phase shift values and the calculated density values can be determined. Since this correlation depends upon both the structure and geometry of the test shape, and upon the material or materials from which the test shape is constructed, such an analysis must be performed for substantially every desired shape and material in order to obtain these essentially empirical correlations.

In step 4b, any deviation of the measured density of the slice of material from the previous measurement of the density of the previous slice is determined. Such deviations are important because they reveal irregularities in the internal structure of the material. Since such sources of deviations as the presence or absence of a hollow core in the measured slice have already been compensated for, the only remaining source of a deviation is irregularities in the internal structure of the material.

In step 5b, the true density of material is calculated in one of two different ways, depending, upon deviations in the calculated density when comparisons are made between two or more slices. In the first method, the deviation in the calculated densities between a plurality of slices is relatively small, such that a single density value can be used for all subsequent calculations. Alternatively, the deviation between the calculated densities of a plurality of slices is relatively large, such that a plurality of density values, and preferably all density values, are used for the subsequent calculations.

Finally, in step 7, the true density value or values, and the raw moisture value, which is calculated in step 6a, are combined to determine the true moisture value. The equation for calculating the true moisture value includes both the true density and any deviations in the calculated density within the slice, as well as an empirically determined correlation factor. The correlation factor depends upon the type and structure of material, and was empirically determined through experimentation. The true moisture value is then output, for example by displaying on a display unit which could include a video screen, or by other devices for displaying the information. Preferably, any deviations in the internal structure of the material which were found by comparision of the measured phase shifts are also displayed, since such information can be very important to the manufacturer or processor of the material.

Figure 4A:
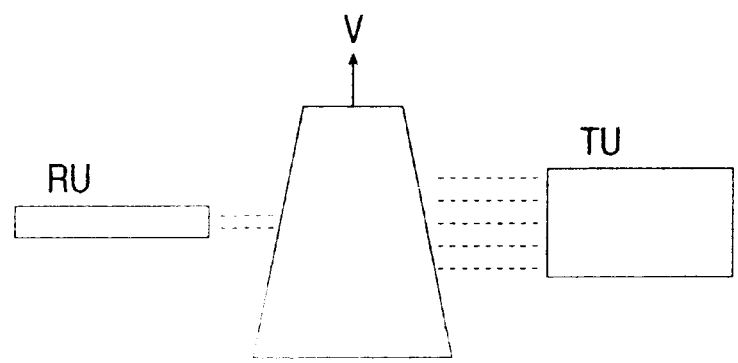
FIGS. 4A and 4B show the agreement between the true moisture content and the moisture content calculated according to FIG. 3.
Figure 4A:
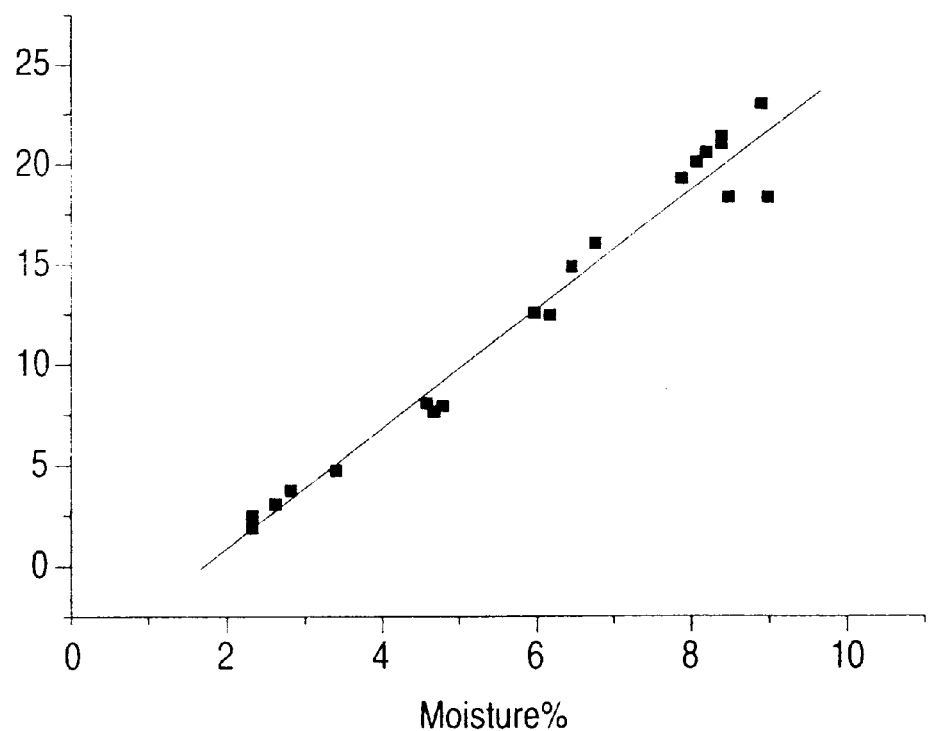
Figure 4B:
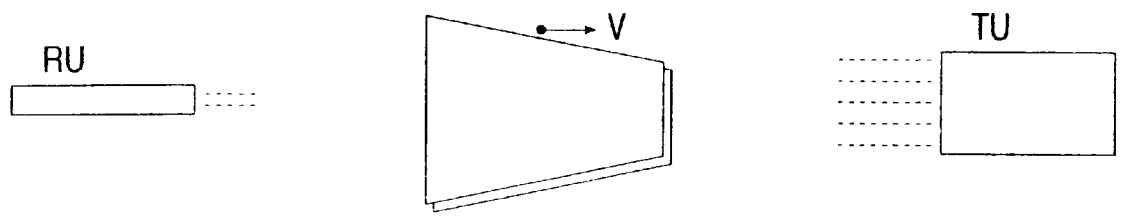
Figure 4B:
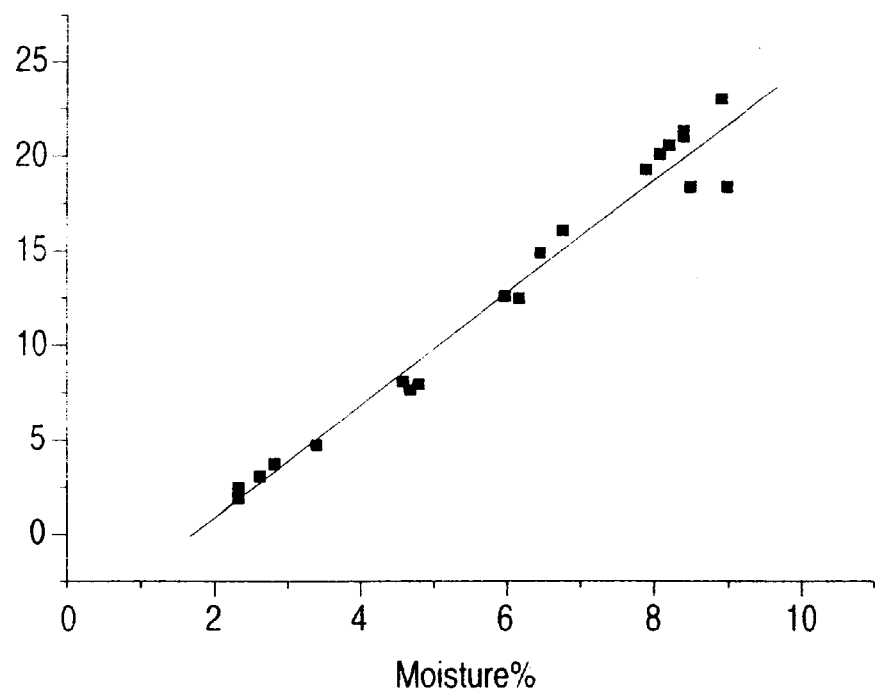

FIGS. 4A and 4B show graphs of the relationship between the true moisture content of the material, as determined by first completely drying the material and then adding a premeasured amount of moisture, and the moisture content calculated according to the method of FIG. 3. To obtain the data shown in FIG. 4A, the bobbin was orthogonal to the transmitting and receiving antennas for the measurements (see FIG. 6A below for an illustration). To obtain the data in FIG. 4B, the bobbin was parallel to the transmitting and receiving antennas for the measurements (see FIG. 5A below for an illustration). In both cases, clearly a linear relationship exists between the true and calculated moisture measurements, showing that the empirical calculations of FIG. 3 are effective.

The calculations described in FIG. 3 are shown in more detail in FIGS. 5 and 6. In FIG. 5, measurements are obtained with the bobbin lying parallel to the antenna and receiver, as shown in FIG. 5A. In FIG. 6, measurements are obtained with the bobbin lying perpendicular to the antenna and receiver, as shown in FIG. 6A. As will become apparent, the position of the bobbin relative to the receiver and antenna has a significant effect on the measurement of the phase shift and of the attenuation.

In FIG. 5A, bobbin 10 is shown lying on its side. Microwave radiation source 28 is on the left of bobbin 10, and receiving antenna 36 is on the right as shown. An arrow shows the direction in which bobbin 10 is moving relative to microwave radiation source 28 and receiving antenna 36. As can be seen, measurements can be obtained from two different types of slices. For example, the slice through points a–a' only includes the material itself, and none of hollow core 12. However, the slice through points b–b' includes hollow core 12. The effect of these two different types of measurements can be clearly seen in FIGS. 5B–5D.

Figure 5B:
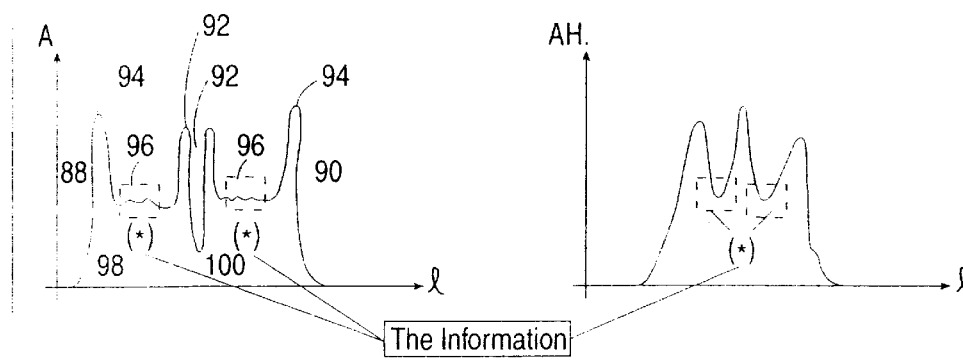

FIG. 5B shows the measured attenuation obtained substantially for all slices along the length, l, of bobbin 10. The measured attenuation can be divided into two portions 88 and 90, separated by a deep trough 92. Each portion has two peaks 94, and a flat section 96. The two peaks 94 represent the first and last measured slices, and are artefactually high. For portion 88, the first slice is measured as bobbin 10 first passes between microwave radiation source 28 and receiving antenna 36, while the last slice is measured as hollow core 10 first passes between microwave radiation source 28 and receiving antenna 36. Neither measurement can be used for determining the corrected attenuation, and hence the raw moisture value, as described in FIG. 3 above, because these measurements are artefacts due to edge effects. Thus, the data points which are used for determining the attenuation for portion 88 are taken from between peaks 94, as shown by box 98.

Deep trough 92 is produced as hollow core 12 passes between microwave radiation source 28 and receiving antenna 36, as for example in the slice taken between points c–c'. The reason for this deep trough 92 is that hollow core 12 contains only or mainly air, so that there is little or no attenuation and/or reflection of the waves which pass through hollow core 12. Of course, measurements taken as the hollow core 12 is between microwave radiation source 28 and receiving antenna 36 are artefactual and cannot be used to determine the moisture content of the material.

Portion 90 of the measured attenuation is produced as the material on bobbin 10 once again passes between microwave radiation source 28 and receiving antenna 36, as for example in slice d–d'. Again, there are two artefactually high peaks from the measurements of the first and last slices. For portion 90, the first slice is measured as hollow core 10 first passes between microwave radiation source 28 and receiving antenna 36, while the last slice is measured as bobbin 10 first passes between microwave radiation source 28 and receiving antenna 36. Again, neither measurement can be used for determining the corrected attenuation, and hence the raw moisture value, as described in FIG. 3 above, because these measurements are artefacts due to edge effects. Thus, the data points which are used for determining the attenuation for portion are taken from between peaks 94, as shown by box 100.

Figure 5C:
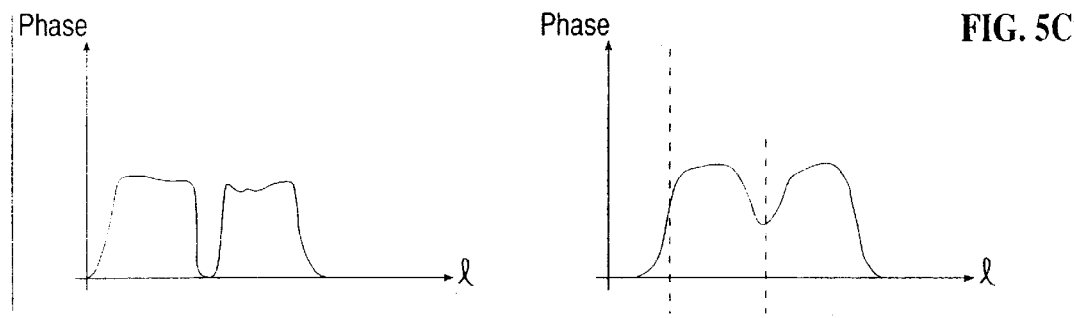

FIG. 5C shows the measured phase shift obtained substantially for all slices along the length, l, of bobbin 10. The phase shift first rises as the first slice is measured, and then remains steady until hollow core 12 passes between microwave radiation source 28 and receiving antenna 36, when it drops substantially. This drop is caused by the fact that hollow core 12 contains relatively less dense air, rather than material. As hollow core 12 leaves the area between microwave radiation source 28 and receiving antenna 36, the phase shift rises again and remains steady until bobbin 10 leaves the area between microwave radiation source 28 and receiving antenna 36. Similarly to the attenuation, the data points which are used for determining the phase shift are taken from between the peaks.

Figure 5D:
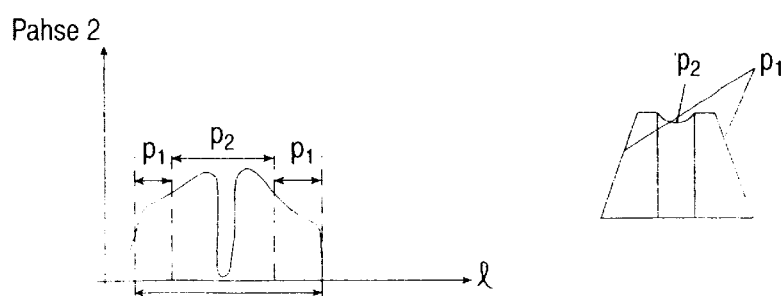

FIG. 5D shows an example of the corrected densities through all the slices, corrected as according to the method outlined in FIG. 3. In this example, the density of the material is irregular. The density of material in the outer layers at the sides of bobbin 10 has one value, $\rho 1$, as marked on the graph in FIG. 5D. However, the density of material near hollow core of bobbin 10 is apparently higher, $\rho 2$, as shown on the graph ($\rho 2>>\rho 1$). Thus, the internal structure of the material is not regular, which can be detected by measurements of the phase shift.

Figure 6A:
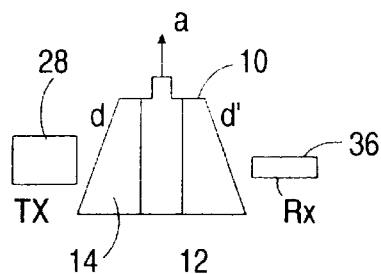
FIGS. 6A–6D show the calculations of FIG. 3 in treater detail for a perpendicular bobbin.

In FIG. 6A, bobbin 10 is shown substantially perpendicular to microwave radiation source and receiver antenna. Microwave rays pass through bobbin 10 in slices such as that taken through points d–d'. In that slice, the rays first pass through layers of material 14, then through hollow core, and again through layers of material 14. However, the total amount of material is greater at the bottom of bobbin 10 than at the top since the shape of bobbin 10 is substantially that of a cone. As shown in FIG. 6A, measurements start at the top of bobbin 10 and then move along the length of bobbin 10 to the bottom.

Figure 6B:
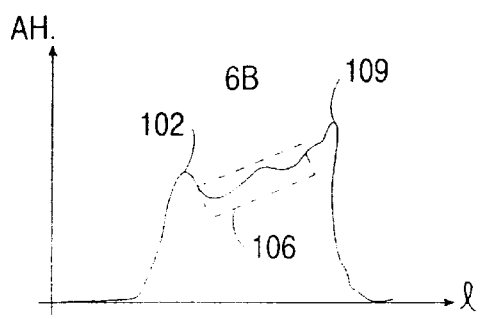

FIG. 6B shows the measured attenuation obtained substantially for all slices along the length, l, of bobbin 10. As noted above, the total amount of material is greater at the bottom of bobbin 10, so that the measured attenuation increases along the length of bobbin 10. The two peaks 102 and 104 represent the first and last measured slices, and are artefactually high. The first slice is measured as bobbin 10 first passes between microwave radiation source 28 and receiving antenna 36, while the last slice is measured as bobbin 10 leaves the area between microwave radiation source 28 and receiving antenna 36. Neither measurement can be used for determining the corrected attenuation, and hence the raw moisture value, as described in FIG. 3 above, because these measurements are artefacts due to edge effects. Thus, the data points which are used for determining the attenuation are taken from between peak 102 and peak 104, as shown by box 106.

Figure 6C:
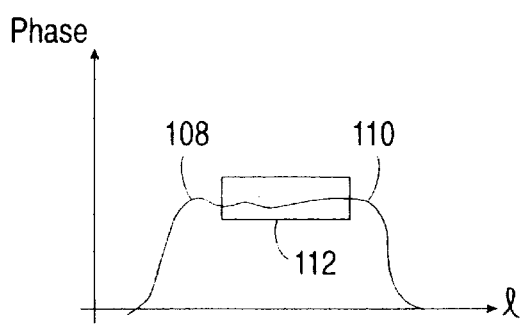

Similarly, FIG. 6C shows the measured phase shift obtained substantially for all slices along the length, l, of bobbin 10. The phase shift first rises as the first slice is measured, and then remains steady until bobbin 10 leaves the area between microwave radiation source 28 and receiving antenna 36. Similarly to the attenuation, the data points which are used for determining the phase shift are taken from between peak 108 and peak 110, as shown by box 112.

Figure 6D:
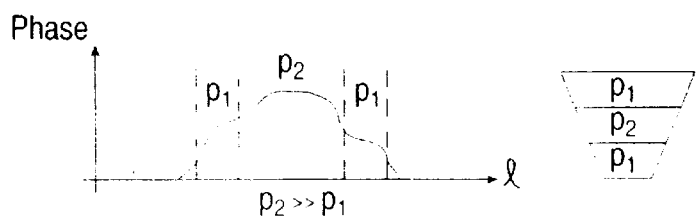

FIG. 6D shows an example of the corrected densities through all the slices, corrected as according to the method outlined in FIG. 3. In this example, the density of the material is irregular. The density of material at the top and at the bottom of bobbin 10 has one value, $\rho 1$, as marked on the graph in FIG. 6D. However, the density of material in the middle of bobbin 10 is apparently higher, $\rho 2$, as shown on the graph ($\rho 2>>\rho 1$). Thus, the internal structure of layers 14 is not regular, which can be detected by measurements of the phase shift.

FIGS. 7A and 7B demonstrate the importance of selecting a particular portion of the measured attenuation for calculating the moisture of the material. In FIG. 7A, the curve shows the relationship between the true moisture values (X-axis) and the measured attenuation obtained from one of the artefactually high peaks described in FIGS. 5 and 6 (Y-axis). Clearly, there is no correlation between the actual moisture content of the material and the artefactual measurements obtained from the peaks. By contrast, FIG. 7B shows the relationship between the true moisture values (X-axis) and the measured attenuation (Y-axis) obtained from the area between the peaks, as for example box 106. The correlation is clearly very high, since the true moisture and the measured attenuation rise in a nearly linear fashion. Thus, the measured attenuation is only an accurate reflection of the true moisture in particular portions of the measurements, for example box 106 of FIG. 6B.

Figure 8:
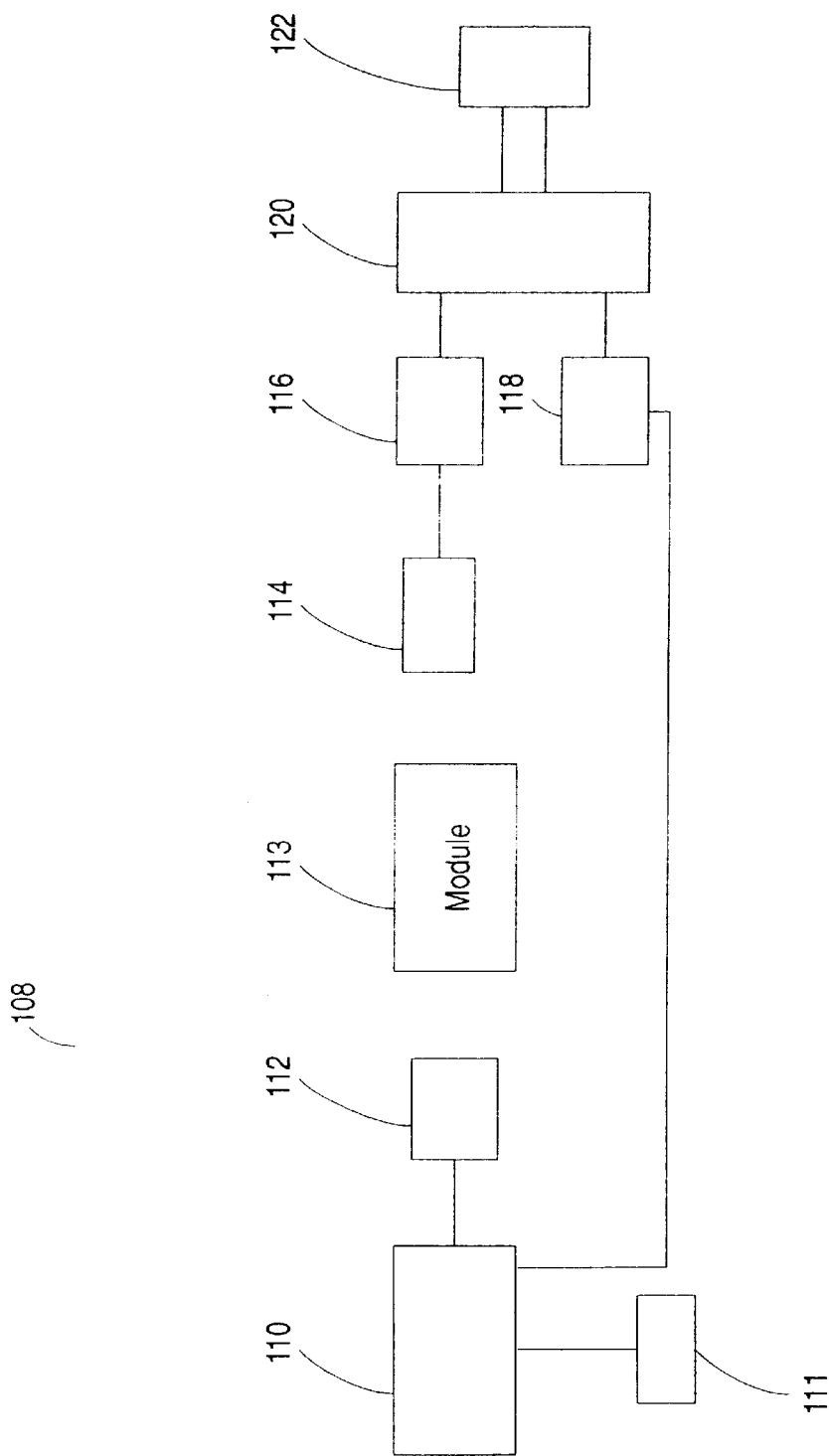
FIG. 8 shows a second exemplary embodiment of a device which can be used with the method of the present invention.

FIG. 8 shows a schematic diagram of another preferred embodiment of the present invention, in which the system of FIG. 1 has been adjusted to permit transmission of more than one frequency of microwave radiation. It should be noted that this preferred embodiment can be used to determine the moisture content of material having substantially any structure as encompassed by the term "module", including bales, bobbins and/or any other bulk of material. Thus, a module can have a substantially irregular structure with variable density.

A multiple-frequency system 108 has a multiple-frequency transmitter 110 for sequentially transmitting microwave radiation at a plurality of frequencies. The frequency to be transmitted is selected by a frequency controller 112. Transmitter 110 then causes a transmitting antenna 112 to transmit microwave radiation at the desired frequency. The transmitted microwave radiation then passes through a module or bale of material (not shown) and is received by a receiving antenna 114. Receiving antenna 114 sends a signal to a signal receiver 116. Signal receiver 116 is preferably a hetrodyne receiver. Substantially simultaneously, a reference signal is sent from transmitter 110 to a reference receiver 118, which is also preferably a hetrodyne receiver. Signal receiver 116 sends a measurement signal (labelled as "I.F. 1") to a detector 120, while reference receiver 118 sends a reference signal (labelled as "I.F. 2") to detector 120. Detector 120 uses the reference signal to determine the correct attenuation of the measurement signal, and then passes both signals to a phase detector 122, which determines the correct phase shift for the measurement signal.

The gross phase shift difference between two phase shifts measured after microwave radiation of two different frequencies has been transmitted through the material can be described as follows.

$$\Delta P(\text{gross}) = F_2/(F_2 - F_1) * (P_2 - P_1)$$

The final phase shift difference is:

$$\Delta P(\text{final}) = Pi + Pg \bmod(\pi)$$

Thus, the gross phase shift difference is obtained by sequentially transmitting microwave radiation of at least two different frequencies, and "hopping" or alternating at least between these two frequencies at each point in the material.

The equations which describe the phase shift and attenuation are as follows.

1. $\lambda = C/F$; $l$ = (path length of radiation);

$\varepsilon'$ = (dielectric constant of material)

2. $P_1 = \dfrac{2\pi}{\lambda_1} \sqrt{\varepsilon'}\, l$;

3. $P_1 = \dfrac{2\pi}{\lambda_2} \sqrt{\varepsilon'}\, l$;

4. $P_1 = KF_1$; $P_2 = KF_2$; $K = \dfrac{2\pi}{C}\sqrt{\varepsilon'}\, l$; $P_1 - P_2 = \Delta P = K(F_1 - F_2)$;

5. $P_1 = Ph_{(t)}(F_1)$; $P_2 = Ph_{(t)}(F_2)$;

6. $K = \dfrac{P_1 - P_2}{F_1 - F_2}$; $(F_1 > F_2)$

7. $Pg$ = (phase including $n\pi$ term) = $K \cdot F_i$ ($i$ is 1 or 2)

8. Corrected Phase-shift = $(Pg - n\pi) + \dfrac{P_1 - P_2}{2}$;

$n = (Pg - n\pi > 0)$

Note that F is the frequency of the microwave radiation; l is the length of the beam path as it passes through the material of the module; $\varepsilon'$ is the dielectric constant of the bulk of material; $P_1$ is the phase deviation for microwave radiation at frequency $F_1$; $P_2$ is the phase deviation for microwave radiation at frequency $F_2$; K $(F_1-F_2)$ is the difference between the phase deviation of the radiation at frequencies $F_1$ and $F_2$; $P_{h(t)}$ is the true phase shift, such that the measured phase shift, $P_1$, is a function of the true phase shift and of the frequency $F_1$, for example; Pg is the gross phase shift difference; and n is the largest number which satisfies equation 8 such that Pg−n$\pi$ is greater than 0.

Although these equations both describe the corrected phase shift and can be used for its calculation, the refinements of the calculations must be done according to empirically observed properties of the material itself and effects of the surrounding environment. FIG. 9 shows a flow chart of these empirically-based calculations. In step 1, a plurality of frequencies of microwave radiation are sequentially transmitted through the material in a module. In step 2, the attenuation and the corrected phase shift are calculated for the plurality of frequencies of microwave radiation.

In step 3, an algorithm is performed to filter noise from the calculated values of the attenuation and the corrected phase shift. The attenuation for a frequency $F_{2i}$ can be described as $A_{21}=a_1 A_{1i}+b_1$. Similarly, the phase shift is $P_{i2}=a_2 P_{1i}+b_2$. Note that $A_{1i}$ and $P_{1i}$ are the attenuation and phase shift values obtained from the previously measured frequency $F_{1i}$. The values for $a_1$, $a_2$, $b_1$ and $b_2$ are taken from a database, depending upon the particular application and material. For example, one set of values would be required for cotton in a bale, while another set of values would be required for a loose pile of synthetic fibers. These values are empirically determined based upon empiric measurements of the material concerned. This calculation to filter noise is preferably performed upon all calculated values of the attenuation and the corrected phase shift. In addition, the value of each of the plurality of frequencies is used for these calculations, since the attenuation and phase shift values are also dependent upon the frequency of the microwave radiation.

Preferably, any "edge" measurements, or measurements made when an edge of material was passing through the beam of microwave radiation, are eliminated from any subsequent calculations since these measurements are artefactual. The determination of whether a particular measurement is an "edge" measurement can be made in a number of ways. For example, the location of the module relative to the beam can be determined, such that when an edge of the module is about to pass through the beam, a signal can be sent to the attenuation and phase shift determiners. Alternatively and preferably, the measurement of the attenuation can be plotted, and any artefactually high peaks or low troughs of attenuation can be eliminated, for example by removing any values which are more than two or three standard deviations from the average attenuation. Thus, any artefactual "edge" measurements are preferably eliminated at this stage of the analysis.

In step 4, the density and the moisture content of the material are calculated from the plurality of filtered attenuation and filtered phase shift values, preferably from all of these values. The moisture content of the material is determined from the following equation:

$$W_\% = \sum_{i=1}^{n} W_i * r_i$$

in which $r_i$ is the correlation factor described previously. The term $W_i$ is a function of the attenuation $A_2$ and the phase shift $P_2$ as determined in step 3, as well as of the type and structure of material. The correlation factor is obtained from a database of these values, determined from empiric observation.

The density of the material is then calculated from a statistical function of the sum of the phase shift values, again taken from the database. This function depends upon the characteristics of the material being analyzed, as for the calculation to filter noise described for step 3. Also, the density is a function of both $P_2$ as determined in step 3, and the type and structure of the material. Thus, the necessary information is taken from a database of empirically determined information.

Preferably, at this stage any defects in the material are detected by examining the densities collected for a portion of the material. The defect could include an irregular moisture distribution within the interior of the material, such as an unusually high moisture content within the material, and the presence of a foreign body inside the material, for example.

In step 5, the temperature of the material is preferably compensated for in the determination of the moisture content and density, if necessary. Again, the necessity for step 5 is determined at least partially accoriding to empiric observations.

In step 6, the moisture content and the density of the material is output, for example to a display on a computer screen or by printing onto paper.

The advantages of determining the moisture content and density of each point in a material at more than one frequency of microwave radiation are as follows. First, measuring the attenuation and phase shift at one point in the material but with more than one frequency permits averaging of the values to obtain a more accurate result. Second, the change in the attenuation is linear, so that alterations in the attenuation due to the measurement at different frequencies can be easily calculated. Any remaining differences are then removed by averaging. Third, a good range of frequencies for any particular type or form of material can be selected, rather than relying upon a single frequency. Finally, measurements at the chosen range of frequencies also enable the true phase shift to be determined.

The third point, the ability to choose a good range of frequencies for a particular type or form of material, is particularly important for mixed materials, or materials containing more than one type of substance. For example, seeds often are mixed with weeds, stems and leaves, which affect the measured moisture content of the seeds themselves. Additionally, this mixture of different types of materials with different properties causes harmonics to appear in the transmitted microwaves. However, the true phase shift can be determined from a linear portion of the curve of phase shift plotted against frequency. Thus, using a plurality of frequencies can simplify the determination of the phase shift for mixed materials.

Optionally and preferably, a frequency range of microwave radiation can be chosen which minimizes reflection of radiation from the material and maximizes transmission of microwave radiation through the material. More preferably, a range of suitable frequencies is chosen from a database before the measurements are made. The choice of a particular range is empirically based on such factors as the type of material and the structure of material. Therefore, cotton in a bale would require a different range of frequencies than yarn on a bobbin, for example. As the measurements are made, the frequency range can also be selected to reduce or eliminate ambient noise from environmental interference. An example of such interference could be a cellular phone for example. Preferably, more than one frequency range is examined before selecting a particular range in which to make the measurements, in order to reduce or eliminate this problem.

In addition, preferably adjustments are made to the selected range of frequencies, such that more measurements are made within a smaller range of frequencies which gives the best results. Thus, adjustments to the frequency range made "on the fly" enable the most sensitive and accurate measurements to be made.

While the invention has been described with respect to a limited number of embodiments, it will be appreciated that many variations, modifications and other applications of the invention may be made.

What is claimed is:

1. A method of determining a moisture content of material on a bobbin featuring a hollow core, the method comprising the steps of:

(a) transmitting a microwave beam substantially through at least a portion of the bobbin, such that said microwave beam is a transmitted microwave beam;

(b) receiving said transmitted microwave beam to form a received microwave beam;

(c) determining a phase shift and an attenuation from said received microwave beam;

(d) repeating steps (a) to (c) for at least a portion of the material on the bobbin, such that a plurality of phase shifts and a plurality of attenuations is obtained;

(e) using at least one empirical factor to correct said plurality of attenuations, producing a plurality of corrected attenuations;

(f) calculating a raw moisture content of the material from said corrected attenuations;

(g) compensating for the presence of the core by using a previously obtained characterization of the core during a calibration step to form a plurality of corrected phase shifts;

(h) determining a density of the material from said corrected phase shifts; and (i) calculating a final moisture content of the material from said density and from said raw moisture content.

2. The method of claim 1, wherein the material features an internal structure and an irregularity of said density of said internal structure is calculated by comparing one of said plurality of corrected phase shifts to a previous value of said corrected phase shifts, such that said irregularity is detected if one of said plurality of corrected phase shifts differs from said previous value.

3. The method of claim 2, wherein said irregularity of said density of said internal structure indicates that the material on the bobbin is of more than one type.

4. The method of claim 1, wherein said at least one empirical factor is a plurality of empirical factors selected from the group consisting of weight of the bobbin, type of the material, structure of the bobbin, location of the bobbin relative to said plurality of microwaves and temperature, and said factors are stored in a database.

5. The method of claim 1, wherein said plurality of corrected attenuations is further corrected by removing attenuations produced after said microwave beam passes through at least a portion of the hollow core.

6. The method of claim 1, wherein the material is selected from the group consisting of cotton fiber, silk fiber, wool fiber, pharmaceutical material, seeds, paper and synthetic fiber.

7. The method of claim 1, wherein the bobbin has a plurality of cores, and a structure and a density of the material are irregular.

8. The method of claim 1, wherein said corrected attenuations and said corrected phase shifts are further corrected by removing attenuations and phase shifts produced after said microwave beam passes through an edge of the bobbin, such that a first portion of said microwave beam passes through said portion of the bobbin and a second portion of said microwave beam substantially does not pass through said portion of the bobbin.

9. The method of claim 1, wherein the step of determining said density includes detecting a defect in the material, said defect being selected from the group consisting of irregular moisture distribution within an interior of the material and presence of a foreign body inside the material.

* * * * *